US009370490B2

(12) United States Patent
Kurti, Jr. et al.

(10) Patent No.: US 9,370,490 B2
(45) Date of Patent: Jun. 21, 2016

(54) METHODS FOR THE PRODUCTION, MODIFICATION AND USE OF METALLIC NANOPARTICLES

(71) Applicant: LOMA LINDA UNIVERSITY, Loma Linda, CA (US)

(72) Inventors: Ralph S. Kurti, Jr., Phelan, CA (US); Christopher C. Perry, Loma Linda, CA (US); Theodore Sabir, Upland, CA (US)

(73) Assignee: Loma Linda University, Loma Linda, CA (US)

( * ) Notice: Subject to any disclaimer, the term of this patent is extended or adjusted under 35 U.S.C. 154(b) by 0 days.

(21) Appl. No.: 14/364,274

(22) PCT Filed: Feb. 28, 2013

(86) PCT No.: PCT/US2013/028422

§ 371 (c)(1),
(2) Date: Jun. 10, 2014

(87) PCT Pub. No.: WO2013/130881

PCT Pub. Date: Sep. 6, 2013

(65) Prior Publication Data

US 2014/0342005 A1  Nov. 20, 2014

Related U.S. Application Data

(60) Provisional application No. 61/604,354, filed on Feb. 28, 2012.

(51) Int. Cl.

| | | |
|---|---|---|
| *A61B 6/02* | (2006.01) | |
| *A61K 9/14* | (2006.01) | |
| *A61K 9/51* | (2006.01) | |
| *B01J 13/22* | (2006.01) | |
| *A61K 47/48* | (2006.01) | |
| *A61K 33/26* | (2006.01) | |
| *B82Y 5/00* | (2011.01) | |
| *A61K 33/24* | (2006.01) | |
| *A61K 33/30* | (2006.01) | |
| *A61K 33/34* | (2006.01) | |
| *A61K 33/38* | (2006.01) | |

(52) U.S. Cl.
CPC ............ *A61K 9/14* (2013.01); *A61K 9/5192* (2013.01); *A61K 33/24* (2013.01); *A61K 33/245* (2013.01); *A61K 33/26* (2013.01); *A61K 33/30* (2013.01); *A61K 33/34* (2013.01); *A61K 33/38* (2013.01); *A61K 47/48215* (2013.01); *A61K 47/48861* (2013.01); *A61K 47/48884* (2013.01); *B01J 13/22* (2013.01); *B82Y 5/00* (2013.01)

(58) Field of Classification Search
CPC .............................. A61K 9/5192; B01J 13/22
See application file for complete search history.

(56) References Cited

U.S. PATENT DOCUMENTS

| | | | |
|---|---|---|---|
| 6,740,338 B1 | 5/2004 | Chopra | |
| 2001/0041991 A1 | 11/2001 | Segal et al. | |
| 2008/0311207 A1 | 12/2008 | Varshney et al. | |
| 2009/0110642 A1 | 4/2009 | Woo et al. | |
| 2009/0324494 A1 | 12/2009 | Ham et al. | |
| 2010/0323884 A1 | 12/2010 | Roldan Cuenya et al. | |
| 2012/0045398 A1* | 2/2012 | Poselt et al. ............... | 424/9.322 |

FOREIGN PATENT DOCUMENTS

| | | |
|---|---|---|
| EP | WO2012007567 A1 | 1/2012 |
| GB | WO2011154711 A1 | 12/2011 |
| RU | 2329074 C1 | 7/2008 |
| WO | WO2010120336 A1 | 10/2010 |
| WO | WO2011163136 A2 | 12/2011 |

OTHER PUBLICATIONS

Loma Linda University, International Search Report and Written Opinion of the International Searching Authority, dated Jul. 29, 2013 for parent International Patent Application No. PCT/US2013/028422.
Loma Linda University, International Preliminary Report on Patentability, dated Mar. 18, 2014 for parent International Patent Application No. PCT/US2013/028422.
Niesz et al., "Precise Control of the Pt Nanoparticle Size by Seeded Growth Using EO13PO30EO13 Triblock Copolymers as Protective Agents," Nano Letters, vol. 5, No. 11, Sep. 27, 2005.

* cited by examiner

*Primary Examiner* — Carlos Azpuru
(74) *Attorney, Agent, or Firm* — Knobbe, Martens, Olson & Bear, LLP

(57) ABSTRACT

A method for producing triblock copolymer-coated metallic nanoparticle seeds which increases the size and shape homogeneity of the triblock copolymer-coated metallic nanoparticle seeds. A quantity of triblock copolymer-coated metallic nanoparticle seeds. A method for producing triblock copolymer-coated metallic nanoparticles which increases the size and shape homogeneity of the triblock copolymer-coated metallic nanoparticles. A quantity of triblock copolymer-coated metallic nanoparticles. A method for producing modified metallic nanoparticles which increases the size and shape homogeneity of the modified metallic nanoparticles. A quantity of modified metallic nanoparticles.

38 Claims, No Drawings

METHODS FOR THE PRODUCTION, MODIFICATION AND USE OF METALLIC NANOPARTICLES

CROSS-REFERENCE TO RELATED APPLICATIONS

The present Application is a national stage of International Patent Application No. PCT/US2013/028422 titled "Methods for the Production, Modification and Use of Metallic Nanoparticles" filed Feb. 28, 2013, which claims the benefit of U.S. Provisional Patent Application No. 61/604,354, titled "Methods for the Production, Modification and Use of Metallic Nanoparticles," filed Feb. 28, 2012, the contents of which are incorporated in this disclosure by reference in their entirety.

STATEMENT REGARDING FEDERALLY SPONSORED RESEARCH OR DEVELOPMENT

This invention was made with United States Government support under U.S. Army Medical Research Acquisition Activity Cooperative Agreement Number DAMD 17-97-2-7016 with the National Medical Technology Testbed, Inc., United States Department of the Army. The United States Government has certain rights in this invention.

BACKGROUND

Metallic nanoparticles, such as, for example, gold nanoparticles (AuNP), have many known and potential uses. The use of metallic nanoparticles, however, is somewhat limited by two disadvantages. First, currently known triblock copolymer (TBP) facilitated methods for producing metallic nanoparticles result in considerable size and shape heterogeneity of the metallic nanoparticles. Metallic nanoparticles of different sizes and shapes have different properties which limit the use of metallic nanoparticles produced by currently known methods. Second, the modification of the metallic nanoparticles by currently known methods, such as, for example, ligating the metallic nanoparticles with organic functional groups, is both time-consuming and complex, making modified metallic nanoparticles produced by currently known methods expensive to produce and, hence, to use.

Therefore, there is a need for a new method for the production of metallic nanoparticles which increases the size and shape homogeneity of the particles as compared to metallic nanoparticles produced by currently known methods. Second, there is a need for a new method for producing modified metallic nanoparticles which is more efficient than currently known methods.

SUMMARY

According to one embodiment of the present invention, there is provided a method for producing triblock copolymer coated metallic nanoparticle seeds which increases the size and shape homogeneity of the triblock copolymer coated metallic nanoparticle seeds, where the triblock copolymer coated metallic nanoparticle seeds comprise a triblock copolymer portion and a metallic portion. The method comprises: a) providing triblock copolymers; b) providing metallic substrate comprising a metal having at least two oxidation states, a lowest oxidation state and a higher oxidation state, where at least some of the metal is in the higher oxidation state; c) making an aqueous solution of the triblock copolymers and water; d) adding a reducing agent to the solution, where the reducing agent reduces the metal in the metallic substrate in the solution from the higher oxidation state to the lowest oxidation state of the metal, or to an oxidation state that is unstable and that reverts to the lowest oxidation state of the metal without further chemical modification; e) adding the metallic substrate to the solution thereby creating a concentration of metallic substrate in the solution; and f) allowing the solution to remain a sufficient time to allow formation of the triblock copolymer coated metallic nanoparticle seeds. In one embodiment, the triblock copolymers are selected from the group consisting of one or more than one of L31 (MW 1100), L43 (MW 1850), L44 (MW 2200), L62 (MW 2500), P84 (MW 4200), P85 (MW 4600), P123 (MW 5760), F68 (MW 8400), F88 (MW 11400), F127 (MW 12600), F108 (MW 14600), and a combination of the preceding. In one embodiment, the triblock copolymers comprise F127 (12600). In one embodiment, the metal is selected from the group consisting of Ag, Au, Bi, Cu, Fe, Ni, Ti and Zn. In one embodiment, the metallic substrate is a salt of the metal. In a preferred embodiment, the metallic substrate is selected from the group consisting of $AgNO_3$, $CuBr_2$, $CuCl_2$, $CuF_2$, $CuI_2$, $CuSO_4$ and $HAuCl_4$. In a particularly preferred embodiment, the metallic substrate is $HAuCl_4$. In one embodiment, the triblock copolymers comprise one or more than one high molecular weight triblock copolymer (MW>4000). In a preferred embodiment, the one or more than one high molecular weight triblock copolymer is selected from the group consisting of one or more than one of P84 (MW 4200), P85 (MW 4600), P123 (MW 5760), F68 (MW 8400), F88 (MW 11400), F127 (MW 12600), F108 (MW 14600), and a combination of the preceding. In one embodiment, the water is deionized water. In one embodiment, the method further comprises adding one or more than one low molecular weight triblock copolymer (MW≤2500) to the solution. In a preferred embodiment, the one or more than one low molecular weight triblock copolymer added to the solution is selected from the group consisting of L31 (MW 1100), L43 (MW 1850), L44 (MW 2200), L62 (MW 2500), and a combination of the preceding. In one embodiment, the reducing agent is L-ascorbic acid. In one embodiment, the reducing agent is an analog of L-ascorbic acid. In one embodiment, the analog of L-ascorbic acid is selected from the group consisting of ascorbyl palmitate and magnesium ascorbyl phosphate. In one embodiment, the reducing agent is added to the solution in a higher concentration than the concentration of the metal substrate in the solution. In one embodiment, the reducing agent is added to the solution at a concentration of at least 1.5 times the concentration of the metal substrate. In one embodiment, the reducing agent is added to the solution at a concentration of at least 2 times the concentration of the metal substrate. In one embodiment, the reducing agent is added to the solution at a concentration of at least 2.5 times the concentration of the metal substrate. In one embodiment, the reducing agent is added to the solution at a concentration of at least 3 times the concentration of the metal substrate. In one embodiment, the metallic substrate is selected from the group consisting of $AgNO_3$, $CuBr_2$, $CuCl_2$, $CuF_2$, $CuI_2$, $CuSO_4$ and $HAuCl_4$. In one embodiment, the metallic substrate is $HAuCl_4$. In one embodiment, the method further comprises harvesting the triblock copolymer coated metallic nanoparticle seeds. In one embodiment, the method further comprises characterizing the triblock copolymer coated metallic nanoparticle seeds.

According to another embodiment of the present invention, there is provided a quantity of triblock copolymer coated metallic nanoparticle seeds, where the triblock copolymer coated metallic nanoparticle seeds have a median maximum particle diameter size standard deviation of +/−25% of the median maximum particle diameter size by electron microscopy. According to another embodiment of the present invention, there is provided a quantity of triblock copolymer coated metallic nanoparticle seeds, where the triblock copolymer coated metallic nanoparticle seeds have a median maximum particle diameter size standard deviation of +/−20% of the median maximum particle diameter size by electron microscopy. According to another embodiment of the present invention, there is provided a quantity of triblock copolymer coated metallic nanoparticle seeds, where the triblock copolymer coated metallic nanoparticle seeds have a median maximum particle diameter size standard deviation of +/−15% of the median maximum particle diameter size by electron microscopy. According to another embodiment of the present invention, there is provided a quantity of triblock copolymer coated metallic nanoparticle seeds, where the triblock copolymer coated metallic nanoparticle seeds have a median maximum particle diameter size standard deviation of +/−10% of the median maximum particle diameter size by electron microscopy. According to another embodiment of the present invention, there is provided a quantity of triblock copolymer coated metallic nanoparticle seeds, where the triblock copolymer coated metallic nanoparticle seeds have a median maximum particle diameter size standard deviation of +/−5% of the median maximum particle diameter size by electron microscopy. In one embodiment, the triblock copolymer coated metallic nanoparticle seeds have a median maximum particle diameter size of between 1 nm and 20 nm. In one embodiment, the quantity of triblock copolymer coated metallic nanoparticle seeds have a median maximum particle diameter size of between 5 nm and 15 nm. In one embodiment, the triblock copolymer coated metallic nanoparticle seeds have a median maximum particle diameter size of between 8 nm and 12 nm. In one embodiment, the triblock copolymer coated metallic nanoparticle seeds have a median maximum particle diameter size of 10 nm with a standard deviation of +/−1 nm by electron microscopy. In one embodiment, the triblock copolymer coated metallic nanoparticle seeds have a number density of between $0.1 \times 10^{11}$ particles/mL and $10 \times 10^{11}$ particles/mL In one embodiment, the triblock copolymer coated metallic nanoparticle seeds have a number density of between $0.5 \times 10^{11}$ particles/mL and $5 \times 10^{11}$ particles/mL In one embodiment, the triblock copolymer coated metallic nanoparticle seeds have a number density of between $1 \times 10^{11}$ particles/mL and $5 \times 10^{11}$ particles/mL In one embodiment, the triblock copolymer coated metallic nanoparticle seeds have a number density of $3 \times 10^{11}$ particles/mL In a preferred embodiment, the triblock copolymer coated metallic nanoparticle seeds are produced according to a method of the present invention. In one embodiment, the triblock copolymer portion of the triblock copolymer coated metallic nanoparticle seeds is selected from the group consisting of one or more than one of L31 (MW 1100), L43 (MW 1850), L44 (MW 2200), L62 (MW 2500), P84 (MW 4200), P85 (MW 4600), P123 (MW 5760), F68 (MW 8400), F88 (MW 11400), F127 (MW 12600), F108 (MW 14600), and a combination of the preceding. In one embodiment, the metallic portion comprises a metal forming the metallic moiety in transition metals and their oxides selected from the group consisting of Ag, $Bi_2O_3$, CuO, $Fe_xO_y$, NiO, $TiO_2$ and ZnO. In one embodiment, the metallic portion comprises gold.

According to another embodiment of the present invention, there is provided method for producing triblock copolymer coated metallic nanoparticles which increases the size and shape homogeneity of the triblock copolymer coated metallic nanoparticles, where the triblock copolymer coated metallic nanoparticles comprise a triblock copolymer portion and a metallic portion. The method comprises: a) providing metallic nanoparticle seeds made according to the present invention, providing triblock copolymers, and providing metallic substrate comprising a metal; b) making a solution of the metallic nanoparticle seeds and the triblock copolymers; c) adding the metallic substrate to the solution; and d) chemically reducing the metallic substrate in the presence of the triblock copolymers and metallic nanoparticle seeds to produce the triblock copolymer coated metallic nanoparticles. In one embodiment, the triblock copolymer portion of the triblock copolymer coated metallic nanoparticles is selected from the group consisting of one or more than one of L31 (MW 1100), L43 (MW 1850), L44 (MW 2200), L62 (MW 2500), P84 (MW 4200), P85 (MW 4600), P123 (MW 5760), F68 (MW 8400), F88 (MW 11400), F127 (MW 12600), F108 (MW 14600), and a combination of the preceding. In one embodiment, the triblock copolymer portion of the triblock copolymer coated metallic nanoparticles comprises F127 (12600). In one embodiment, the metallic portion comprises a metal forming the metallic moiety in transition metals and their oxides selected from the group consisting of Ag, $Bi_2O_3$, CuO, $Fe_xO_y$, NiO, $TiO_2$ and ZnO. In one embodiment, the metallic portion comprises gold. In one embodiment, the triblock copolymers provided are selected from the group consisting of one or more than one of L31 (MW 1100), L43 (MW 1850), L44 (MW 2200), L62 (MW 2500), P84 (MW 4200), P85 (MW 4600), P123 (MW 5760), F68 (MW 8400), F88 (MW 11400), F127 (MW 12600), F108 (MW 14600), and a combination of the preceding. In one embodiment, the triblock copolymers provided comprises F127 (12600). In one embodiment, the metal is selected from the group consisting of Ag, Au, Bi, Cu, Fe, Ni, Ti and Zn. In one embodiment, the metallic substrate is a salt of the metal. In one embodiment, the metallic substrate is selected from the group consisting of $AgNO_3$, $CuBr_2$, $CuCl_2$, $CuF_2$, $CuI_2$, $CuSO_4$ and $HAuCl_4$. In one embodiment, the metallic substrate is $HAuCl_4$. In one embodiment, the triblock copolymers comprise one or more than one high molecular weight triblock copolymer (MW>4000). In a preferred embodiment, the one or more than one high molecular weight triblock copolymer is selected from the group consisting of one or more than one of P84 (MW 4200), P85(MW 4600), P123 (MW 5760), F68 (MW 8400), F88 (MW 11400), F127 (MW 12600), F108 (MW 14600), and a combination of the preceding. In a preferred embodiment, the triblock copolymers further comprise one or more than one low molecular weight triblock copolymer (MW≤2500). In one embodiment, the one or more than one low molecular weight triblock copolymer is selected from the group consisting of L31 (MW 1100), L43 (MW 1850), L44 (MW 2200), L62 (MW 2500), and a combination of the preceding. In one embodiment, the method further comprises monitoring the production of the coated metallic nanoparticles. In one embodiment, the method further comprises characterizing the triblock copolymer coated gold nanoparticles.

According to another embodiment of the present invention, there is provided a quantity of triblock copolymer coated metallic nanoparticles, where the triblock copolymer coated metallic nanoparticles have a median maximum particle diameter size standard deviation of +/−25% of the median maximum particle diameter size by electron microscopy. According to another embodiment of the present invention, there is provided a quantity of triblock copolymer coated metallic nanoparticles, where the triblock copolymer coated metallic nanoparticles have a median maximum particle diameter size standard deviation of +/−20% of the median maximum particle diameter size by electron microscopy. According to another embodiment of the present invention, there is provided a quantity of triblock copolymer coated metallic nanoparticles, where the triblock copolymer coated metallic nanoparticles have a median maximum particle diameter size standard deviation of +/−15% of the median maximum particle diameter size by electron microscopy. According to another embodiment of the present invention, there is provided a quantity of triblock copolymer coated metallic nanoparticles, where the triblock copolymer coated metallic nanoparticles have a median maximum particle diameter size standard deviation of +/−10% of the median maximum particle diameter size by electron microscopy. According to another embodiment of the present invention, there is provided a quantity of triblock copolymer coated metallic nanoparticles, where the triblock copolymer coated metallic nanoparticles have a median maximum particle diameter size standard deviation of +/−5% of the median maximum particle diameter size by electron microscopy. In one embodiment, the triblock copolymer coated metallic nanoparticles have a median maximum particle diameter size of between 30 nm and 300 nm. In one embodiment, the triblock copolymer coated metallic nanoparticles have a median maximum particle diameter size of between 30 nm and 100 nm. In one embodiment, the triblock copolymer coated metallic nanoparticles have a median maximum particle diameter size of between 40 nm and 60 nm. In one embodiment, the triblock copolymer coated metallic nanoparticles have a number density of between $0.1 \times 10^{10}$ particles/cm$^3$ and $10 \times 10^{10}$ particles/cm$^3$. In one embodiment, the triblock copolymer coated metallic nanoparticles have a number density of between $0.5 \times 10^{10}$ particles/cm$^3$ and $5 \times 10^{10}$ particles/cm$^3$. In one embodiment, the triblock copolymer coated metallic nanoparticles have a number density of between $1 \times 10^{10}$ particles/cm$^3$ and $5 \times 10^{10}$ particles/cm$^3$. In one embodiment, the triblock copolymer coated metallic nanoparticles have a number density of $1 \times 10^{10}$ particles/cm$^3$. In one embodiment, the triblock copolymer coated metallic nanoparticles are produced according to the method of the present invention. In one embodiment, the triblock copolymer portion of the triblock copolymer coated metallic nanoparticles is selected from the group consisting of one or more than one of L31 (MW 1100), L43 (MW 1850), L44 (MW 2200), L62 (MW 2500), P84 (MW 4200), P85 (MW 4600), P123 (MW 5760), F68 (MW 8400), F88 (MW 11400), F127 (MW 12600), F108 (MW 14600), and a combination of the preceding. In one embodiment, the metallic portion comprises a metal forming the metallic moiety in transition metals and their oxides selected from the group consisting of Ag, $Bi_2O_3$, CuO, $Fe_xO_y$, NiO, $TiO_2$ and ZnO. In one embodiment, the metallic portion comprises gold.

According to another embodiment of the present invention, there is provided a method for producing modified metallic nanoparticles, where the modified metallic nanoparticles comprise a ligand portion and a metallic portion. The method comprises: a) providing triblock copolymer coated metallic nanoparticles made according to the present invention; and b) replacing the triblock copolymer portion with the ligand. According to another embodiment of the present invention, there is provided a method for producing modified metallic nanoparticles, where the modified metallic nanoparticles comprise a ligand portion and a metallic portion. In one embodiment, the ligand portion comprises a small organic molecule. In one embodiment, the ligand portion is selected from the group consisting of one or more than one antibody, metal, peptide, protein, oligonucleotide, thiolated DNA and a combination of the preceding. In one embodiment, the metallic portion of the modified metallic nanoparticles comprises gold.

According to another embodiment of the present invention, there is provided a quantity of modified metallic nanoparticles, where the modified metallic nanoparticles have a median maximum particle diameter size standard deviation of +/−25% of the median maximum particle diameter size by electron microscopy. According to another embodiment of the present invention, there is provided a quantity of modified metallic nanoparticles, where the modified metallic nanoparticles have a median maximum particle diameter size standard deviation of +/−20% of the median maximum particle diameter size by electron microscopy. According to another embodiment of the present invention, there is provided a quantity of modified metallic nanoparticles, where the modified metallic nanoparticles have a median maximum particle diameter size standard deviation of +/−15% of the median maximum particle diameter size by electron microscopy. According to another embodiment of the present invention, there is provided a quantity of modified metallic nanoparticles, where the modified metallic nanoparticles have a median maximum particle diameter size standard deviation of +/−10% of the median maximum particle diameter size by electron microscopy. According to another embodiment of the present invention, there is provided a quantity of modified metallic nanoparticles, where the modified metallic nanoparticles have a median maximum particle diameter size standard deviation of +/−5% of the median maximum particle diameter size by electron microscopy. In one embodiment, the modified metallic nanoparticles have a median maximum particle diameter size of between 30 nm and 300 nm. In one embodiment, the modified metallic nanoparticles have a median maximum particle diameter size of between 30 nm and 100 nm. In one embodiment, the modified metallic nanoparticles have a median maximum particle diameter size of between 40 nm and 60 nm. In one embodiment, the modified metallic nanoparticles have a number density of between $0.1 \times 10^{10}$ particles/cm$^3$ and $10 \times 10^{10}$ particles/cm$^3$. In one embodiment, the modified metallic nanoparticles have a number density of between $0.5 \times 10^{10}$ particles/cm$^3$ and $5 \times 10^{10}$ particles/cm$^3$. In one embodiment, the modified metallic nanoparticles have a number density of between $1 \times 10^{10}$ particles/cm$^3$ and $5 \times 10^{10}$ particles/cm$^3$. In one embodiment, the modified metallic nanoparticles have a number density of $1 \times 10^{10}$ particles/cm$^3$. In one embodiment, the modified metallic nanoparticles are produced according to the method of the present invention. In one embodiment, the triblock copolymer portion of the modified metallic nanoparticles is selected from the group consisting of one or more than one of L31 (MW 1100), L43 (MW 1850), L44 (MW 2200), L62 (MW 2500), P84 (MW 4200), P85 (MW 4600), P123 (MW 5760), F68 (MW 8400), F88 (MW 11400), F127 (MW 12600), F108 (MW 14600), and a combination of the preceding. In one embodiment, the metallic portion comprises a metal forming the metallic moiety in transition metals and their oxides selected from the group consisting of Ag, $Bi_2O_3$, CuO, $Fe_xO_y$, NiO, $TiO_2$ and ZnO. In one embodiment, the metallic portion of the modified metallic nanoparticles comprises gold.

According to another embodiment of the present invention, there is provided a method of using triblock copolymer coated metallic nanoparticles. The method comprises providing the triblock copolymer coated metallic nanoparticles according to the present invention.

According to another embodiment of the present invention, there is provided a method of treating a patient for a condition or disease. The method comprises: a) determining that the patient has a condition or disease suitable for treatment by the administration of triblock copolymer coated metallic nanoparticles; b) providing triblock copolymer coated metallic nanoparticles according to the present invention; and c) administering to the patient one or more than one dose of the triblock copolymer coated metallic nanoparticles by a route, thereby treating the condition or disease. In one embodiment, the patient is a human. In one embodiment, the one or more than one dose administered is between 0.01 ng and 1 gram. In one embodiment, the one or more than one dose administered is between 0.01 ng and 10,000 mg. In one embodiment, the one or more than one dose administered is between 1 ng and 10,000 mg. In one embodiment, the one or more than one dose administered is between 0.1 mg and 10,000 mg. In one embodiment, the one or more than one dose is a plurality of doses. In one embodiment, the plurality of doses is two doses. In one embodiment, the plurality of doses is three doses. In one embodiment, the plurality of doses is four doses. In one embodiment, the plurality of doses is more than four doses. In one embodiment, the plurality of doses is administered between one hour and seventy-two hours apart. In one embodiment, the plurality of doses is administered between one hour and thirty-six hours apart. In one embodiment, the plurality of doses is administered between one hour and twenty-four hours apart. In one embodiment, the route is selected from the group consisting of intrarectal, intramuscular, intraperitoneal, intrathecal, intravenous and oral. In one embodiment, the condition or disease is cancer and administering the triblock copolymer coated metallic nanoparticles decreases the toxicity of radiotherapy being used to treat the cancer. In one embodiment, the ligand portion of the triblock copolymer coated metallic nanoparticles is a delivery vehicle for biologically active agents. In one embodiment, determining that the patient has a condition or disease suitable for treatment by the administration of the triblock copolymer coated metallic nanoparticles comprises diagnosing the patient with a condition or disease suitable for treatment by the method. In one embodiment, diagnosing the patient comprises performing one or more than one of action selected from the group consisting of performing a physical examination, performing a non-invasive imaging examination, and identifying one or more than one marker for the condition or disease in the blood or other body fluid of the patient. In one embodiment, identifying the patient comprises consulting patient records to determine if the patient has a condition or disease suitable for treatment by the method.

According to another embodiment of the present invention, there is provided a method of using modified metallic nanoparticles. The method comprises providing the modified metallic nanoparticles according to the present invention.

According to another embodiment of the present invention, there is provided a method of treating a patient for a condition or disease. The method comprises: a) determining that the patient has a condition or disease suitable for treatment by the administration of modified metallic nanoparticles; b) providing modified metallic nanoparticles according to the present invention; and c) administering to the patient one or more than one dose of the triblock copolymer coated metallic nanoparticles by a route, thereby treating the condition or disease. In one embodiment, the patient is a human. In one embodiment, the one or more than one dose administered is between 0.01 ng and 1 gram. In one embodiment, the one or more than one dose administered is between 0.01 ng and 10,000 mg. In one embodiment, the one or more than one dose administered is between 1 ng and 10,000 mg. In one embodiment, the one or more than one dose administered is between 0.1 mg and 10,000 mg. In one embodiment, the one or more than one dose administered is a plurality of doses. In one embodiment, the plurality of doses is two doses. In one embodiment, the plurality of doses is three doses. In one embodiment, the plurality of doses is four doses. In one embodiment, the plurality of doses is more than four doses. In one embodiment, the plurality of doses is administered between one hour and seventy-two hours apart. In one embodiment, the plurality of doses is administered between one hour and thirty-six hours apart. In one embodiment, the plurality of doses is administered between one hour and twenty-four hours apart. In one embodiment, the route is selected from the group consisting of intrarectal, intramuscular, intraperitoneal, intrathecal, intravenous and oral. In one embodiment, the condition or disease is cancer and administering the triblock copolymer coated metallic nanoparticles decreases the toxicity of radiotherapy being used to treat the cancer. In one embodiment, the ligand portion of the triblock copolymer coated metallic nanoparticles is a delivery vehicle for biologically active agents. In one embodiment, the patient has a condition or disease suitable for treatment by the administration of the triblock copolymer coated metallic nanoparticles and the method further comprises diagnosing the patient with a condition or disease suitable for treatment by the method. In one embodiment, diagnosing the patient comprises performing one or more than one of action selected from the group consisting of performing a physical examination, performing a non-invasive imaging examination, and identifying one or more than one marker for the condition or disease in the blood or other body fluid of the patient. In one embodiment, identifying the patient comprises consulting patient records to determine if the patient has a condition or disease suitable for treatment by the method.

According to another embodiment of the present invention, there is provided a pharmaceutical suitable for treating a patient with a condition or disease. The pharmaceutical comprises triblock copolymer coated metallic nanoparticles according to the present invention. In one embodiment, the pharmaceutical further comprises one or more than one substance selected from the group consisting of a binder, a coloring chemical and a flavoring chemical.

According to another embodiment of the present invention, there is provided a pharmaceutical suitable for treating a patient with a condition or disease. The pharmaceutical comprises modified metallic nanoparticles according to the present invention. In one embodiment, the pharmaceutical further comprises one or more than one substance selected from the group consisting of a binder, a coloring chemical and a flavoring chemical.

DESCRIPTION

According to one embodiment of the present invention, there is provided a method for producing triblock copolymer-coated metallic nanoparticle seeds which increases the size and shape homogeneity of the triblock copolymer coated metallic nanoparticle seeds compared to triblock copolymer-coated metallic nanoparticles produced by currently known methods, where the triblock copolymer-coated metallic nanoparticle seeds comprise a triblock copolymer portion and a metallic portion. In a preferred embodiment, the metallic portion of the triblock copolymer-coated metallic nanoparticle seeds comprises gold. According to another embodiment of the present invention, there is provided a quantity of triblock copolymer-coated metallic nanoparticle seeds having a narrow particle size distribution. In one embodiment, the triblock copolymer-coated metallic nanoparticle seeds having the narrow particle size distribution are produced according to the method for producing triblock copolymer-coated metallic nanoparticle seeds according to the present invention. According to one embodiment of the present invention, there is provided a method for producing triblock copolymer-coated metallic nanoparticles which increases the size and shape homogeneity of the triblock copolymer-coated metallic nanoparticles as compared to triblock copolymer-coated metallic nanoparticles produced by currently known methods, where the triblock copolymer-coated metallic nanoparticles comprise a triblock copolymer portion and a metallic portion. The method comprises providing triblock copolymer-coated metallic nanoparticle seeds according to the present invention. In a preferred embodiment, the metallic portion of the triblock copolymer-coated metallic nanoparticles comprises gold. According to another embodiment of the present invention, there is provided a quantity of triblock copolymer-coated metallic nanoparticles having a narrow particle size distribution. According to one embodiment of the present invention, there is provided a method for producing modified metallic nanoparticles which increases the size and shape homogeneity of the modified metallic nanoparticles as compared to modified metallic nanoparticles produced by currently known methods, where the modified metallic nanoparticles comprise a ligand portion and a metallic portion. The method comprises providing triblock copolymer-coated metallic nanoparticles made according to the present invention. In a preferred embodiment, the ligand portion of the modified metallic nanoparticles is selected from the group consisting of one or more than one antibody, metal, peptide, protein, oligonucleotide, thiolated DNA and a combination of the preceding. In a preferred embodiment, the metallic portion of the modified metallic nanoparticles comprises gold. According to another embodiment of the present invention, there is provided a quantity of modified metallic nanoparticles having a narrow particle size distribution. According to another embodiment of the present invention, there is provided a method of using triblock copolymer-coated metallic nanoparticles or modified metallic nanoparticles, where the method comprises providing triblock copolymer-coated metallic nanoparticles or modified metallic nanoparticles produced according to the present invention. In one embodiment, the method of using comprises treating a patient for a condition or disease. In another embodiment, the method of using comprises decreasing the potential toxicity of radiation administered to the patient. According to another embodiment of the present invention, there is provided a pharmaceutical suitable for treating a patient with a condition or disease. In one embodiment, the pharmaceutical comprises triblock copolymer-coated metallic nanoparticles produced according to the method for producing triblock copolymer-coated metallic nanoparticles of the present invention. In another embodiment, the pharmaceutical comprises modified metallic nanoparticles produced according to the method for producing modified metallic nanoparticles of the present invention. The methods, triblock copolymer-coated metallic nanoparticle seeds, triblock copolymer-coated metallic nanoparticles, modified metallic nanoparticles and pharmaceuticals will now be disclosed in detail.

As used in this disclosure, except where the context requires otherwise, the term "comprise" and variations of the term, such as "comprising," "comprises" and "comprised" are not intended to exclude other additives, components, integers or steps.

As used in this disclosure, except where the context requires otherwise, the method steps disclosed are not intended to be limiting nor are they intended to indicate that each step is essential to the method or that each step must occur in the order disclosed.

As used in this disclosure, gold is used as an example of the metallic portion of the triblock copolymer-coated metallic nanoparticle seeds, the triblock copolymer-coated metallic nanoparticles, the modified metallic nanoparticles and the pharmaceuticals according to the present invention; however, except where the context requires otherwise, the metallic portion of the triblock copolymer-coated metallic nanoparticle seeds, the triblock copolymer-coated metallic nanoparticles, the modified metallic nanoparticles and the pharmaceuticals according to the present invention can be metals other than gold, such as, for example, metals forming the metallic moiety in transition metals and their oxides selected from the group consisting of Ag, $Bi_2O_3$, CuO, $Fe_xO_y$, NiO, $TiO_2$ and ZnO, as will be understood by those with skill in the art with respect to this disclosure.

As used in this disclosure, "triblock copolymers" (TBP, TBPs) means a central hydrophobic chain of polyoxypropylene (poly(propylene oxide); PO) flanked by two hydrophilic chains of polyoxyethylene (poly(ethylene oxide); EO), and are also known as poloxamers, and under the commercial names Kolliphor™ (BASF SE, Ludwigshafen am Rhein, Germany); Pluronic® (BASF Corporation, North Mount Olive, N.J. US) and Synperonic® (Unichema Chemie BV Gouda, Netherlands).

As used in this disclosure, "modified metallic nanoparticles" means triblock copolymer-coated metallic nanoparticles produced according to the present method where the triblock copolymer portion has been replaced with a ligand active for an intended purpose, such as, for example, a moiety selected from the group consisting of one or more than one antibody, metal, peptide, protein, oligonucleotide, thiolated DNA and a combination of the preceding.

As used in this disclosure, "median maximum particle diameter size" means that 50% of the sample has a smaller maximum particle diameter and 50% of the sample has a larger maximum particle diameter as measured by electron microscopy.

According to one embodiment of the present invention, there is provided a method for producing triblock copolymer-coated metallic nanoparticle seeds which increases the size and shape homogeneity of the triblock copolymer-coated metallic nanoparticle seeds compared to triblock copolymer-coated metallic nanoparticles produced by currently known methods, where the triblock copolymer-coated metallic nanoparticle seeds comprise a triblock copolymer portion and a metallic portion. The method comprises: a) providing triblock copolymers; b) providing metallic substrate comprising a metal having at least two oxidation states, a lowest oxidation state and a higher oxidation state, where at least some of the metal is in the higher oxidation state; c) making an aqueous solution of the triblock copolymers and water; d) adding a reducing agent to the solution, where the reducing agent reduces the metal in the metallic substrate in the solution from the higher oxidation state to the lowest oxidation state of the metal, or to an oxidation state that is unstable and that reverts to the lowest oxidation state of the metal without further chemical modification; e) adding the metallic substrate to the solution thereby creating a concentration of metallic substrate in the solution; and f) allowing the solution to remain a sufficient time to allow formation of the triblock copolymer-coated metallic nanoparticle seeds. Put another way, the method for producing triblock copolymer-coated metallic nanoparticle seeds works by altering the equilibrium disproportionation of the metal in a metallic salt in the solution, such as, for example, in the case of gold, by altering the equilibrium disproportionation of Au(I), by adding a reducing agent to precursor solutions that has a standard electrode potential which is weakly positive and less than the electrode potential for Au(III)/Au(I) [Au(III)+2e→Au(I)E=1.4 V] to precursor solutions, where Au(III) is reduced to Au(I) thereby driving the equilibrium to form Au(0). In one embodiment, the metal in a metallic salt in the solution is gold and the reducing agent is L-ascorbic acid, where the electrode potential dihydroascorbic acid/L-ascorbic acid is about 0.2 V for pH values <4. In another embodiment, the reducing agent is an analog of L-ascorbic acid. In one embodiment, the analog of L-ascorbic acid is selected from the group consisting of ascorbyl palmitate and magnesium ascorbyl phosphate.

The method for producing triblock copolymer-coated metallic nanoparticle seeds comprises providing triblock copolymers. In one embodiment, the triblock copolymers are selected from the group consisting of one or more than one of L31 (MW 1100), L43 (MW 1850), L44 (MW 2200), L62 (MW 2500), P84 (MW 4200), P85 (MW 4600), P123 (MW 5760), F68 (MW 8400), F88 (MW 11400), F127 (MW 12600), F108 (MW 14600), and a combination of the preceding. In a preferred embodiment, the triblock copolymers comprises F127 (12600). The triblock copolymers provided can be made according to techniques known to those with skill in the art, or can be purchased from a variety of commercially available sources, such as, for example, Sigma-Aldrich, Milwaukee, Wis. US.

The method further comprises providing metallic substrate comprising a metal having at least two oxidation states, a lowest oxidation state and a higher oxidation state, where at least some of the metal is in the higher oxidation state. In one embodiment, the metal is selected from the group consisting of Ag, Au, Bi, Cu, Fe, Ni, Ti and Zn. In a preferred embodiment, the metallic substrate is a salt of the metal. In one embodiment, the metallic substrate is selected from the group consisting of $AgNO_3$, $CuBr_2$, $CuCl_2$, $CuF_2$, $CuI_2$, $CuSO_4$ and $HAuCl_4$. In a preferred embodiment, the metallic substrate is $HAuCl_4$. The metallic substrate provided can be purchased commercially, such as, for example, from Sigma-Aldrich, Milwaukee, Wis. US. In another embodiment, the metallic substrate is made according to techniques known to those with skill in the art.

Next, the method comprises making an aqueous solution of the provided triblock copolymers and water. In one embodiment, the provided triblock copolymers comprise one or more than one high molecular weight triblock copolymer (MW>4000). In one embodiment, the one or more than one high molecular weight triblock copolymer is selected from the group consisting of one or more than one of P84 (MW 4200), P85(MW 4600), P123 (MW 5760), F68 (MW 8400), F88 (MW 11400), F127 (MW 12600), F108 (MW 14600), and a combination of the preceding. In a preferred embodiment, the solution is made by adding the triblock copolymers to deionized water. As an example, this solution can be made by adding the high molecular weight triblock copolymers to deionized water (Milli-Q water; Millipore, Billerica, Mass. US) to give a final concentration in (weight/volume) % of between 1% (1 g/100 mL) and 5% (5 g/100 mL) In a preferred embodiment, the high molecular weight triblock copolymer is F127 (MW 12600). In another embodiment, the method further comprises adding one or more than one low molecular weight triblock copolymer (MW≤2500) to the solution. The combination of high molecular weight triblock copolymers and low molecular weight triblock copolymers advantageously produces an additional level of control over the triblock copolymer phase behavior, as will be understood by those with skill in the art with respect to this disclosure. In one embodiment, the one or more than one low molecular weight triblock copolymer added to the solution is selected from the group consisting of L31 (MW 1100), L43 (MW 1850), L44 (MW 2200), L62 (MW 2500), and a combination of the preceding. As an example, the solution can be made using F68 as the high molecular weight triblock copolymer and L31 as the low molecular weight triblock copolymer. As an example, the solution can be made by dissolving 10 mL of 50% w/v (50 g/100 mL) F68 and 10 mL L31 in 100 mL of deionized water (Milli-Q water; Millipore, Billerica, Mass. US) to give a final concentration of 8 mM L31 and 4 mM F68. This mixture corresponds to an EO:PO molar ratio of about 0.7. Advantageously, the cloud point (CP) (where the solution phase separates of stock) can be reduced from above 100° C. for aqueous F68 binary mixtures to about 30° C. for aqueous L31/F68 ternary mixtures.

Then, the method comprises adding a reducing agent to the solution, where the reducing agent reduces the metal in the metallic substrate in the solution from the higher oxidation state to the lowest oxidation state of the metal, or to an oxidation state that is unstable and that reverts to the lowest oxidation state of the metal without further chemical modification. When the metal in the metallic portion is gold, the reducing agent has a standard electrode potential that is weakly positive and less than the electrode potential for Au(III)/Au(I) [Au(III)+2e→Au(I) E=1.4 V], where Au(III) is reduced to Au(I) thereby driving the equilibrium to form Au(0). In one embodiment, the reducing agent is L-ascorbic acid (that has an electrode potential dihydroascorbic acid/L-ascorbic acid is about 0.2 V for pH values <4). In another embodiment, the reducing agent is an analog of L-ascorbic acid. In one embodiment, the analog of L-ascorbic acid is selected from the group consisting of ascorbyl palmitate and magnesium ascorbyl phosphate.

In one embodiment, the reducing agent is added to the solution in a higher concentration than the concentration of the metal substrate in the solution. In one embodiment, the reducing agent is added to the solution at a concentration of at least 1.5 times the concentration of the metal substrate. In one embodiment, the reducing agent is added to the solution at a concentration of at least 2 times the concentration of the metal substrate. In one embodiment, the reducing agent is added to the solution at a concentration of at least 2.5 times the concentration of the metal substrate. In one embodiment, the reducing agent is added to the solution at a concentration of at least 3 times the concentration of the metal substrate. In one embodiment, the reducing agent is added to the solution at a concentration of 5 mM.

Next, the method comprises adding the metallic substrate to the solution, thereby creating a concentration of metallic substrate in the solution. In one embodiment, the metallic substrate is selected from the group consisting of $AgNO_3$, $CuBr_2$, $CuCl_2$, $CuF_2$, $CuI_2$, $CuSO_4$ and $HAuCl_4$. In a preferred embodiment, the metallic substrate is $HAuCl_4$. In a preferred embodiment, the metallic substrate is $HAuCl_4$. In a preferred embodiment, the metallic substrate is 0.2 mM $HAuCl_4$. For example, 0.2 mM HAuCl4 was added to 5 mM of the aqueous solution of the triblock copolymer solution and reducing agent.

Then, the method comprises allowing the solution to remain a sufficient time to allow formation of the triblock copolymer-coated metallic nanoparticle seeds, such as, for example, until the solution changed color indicting completion of the formation. In one embodiment, the method further comprises harvesting the triblock copolymer-coated metallic nanoparticle seeds. By way of example, triblock copolymercoated metallic nanoparticle seeds made as disclosed were harvested by first washing by centrifugation (17,900 g; 5 min) and suspended in water in preparation for characterization. Harvested triblock copolymer-coated metallic nanoparticle seeds made according to this method were characterized by electron microscopy and found to have a median maximum particle diameter size of 10 nm with a standard deviation of 1 nm. In another embodiment, the method further comprises characterizing the triblock copolymer-coated gold nanoparticle seeds produced according to the present invention. In one embodiment, characterizing comprises measuring the size of the triblock copolymer-coated metallic nanoparticle seeds using scanning transmission electron microscopy using techniques known to those with skill in the art, as will be understood by those with skill in the art with respect to this disclosure. In another embodiment, characterizing comprises imaging the triblock copolymer-coated metallic nanoparticle seeds using atomic force microscopy (AFM), using techniques known to those with skill in the art, as will be understood by those with skill in the art with respect to this disclosure.

According to another embodiment of the present invention, there is provided a quantity of triblock copolymer-coated metallic nanoparticle seeds. In one embodiment, the triblock copolymer-coated metallic nanoparticle seeds have a median maximum particle diameter size standard deviation of +/−25% of the median maximum particle diameter size by electron microscopy. In one embodiment, the triblock copolymer-coated metallic nanoparticle seeds have a median maximum particle diameter size standard deviation of +/−20% of the median maximum particle diameter size by electron microscopy. In one embodiment, the triblock copolymer-coated metallic nanoparticle seeds have a median maximum particle diameter size standard deviation of +/−15% of the median maximum particle diameter size by electron microscopy. In one embodiment, the triblock copolymer-coated metallic nanoparticle seeds have a median maximum particle diameter size standard deviation of +/−10% of the median maximum particle diameter size by electron microscopy. In one embodiment, the triblock copolymer-coated metallic nanoparticle seeds have a median maximum particle diameter size standard deviation of +/−5% of the median maximum particle diameter size by electron microscopy. In one embodiment, the triblock copolymer-coated metallic nanoparticle seeds have a median maximum particle diameter size of between 1 nm and 20 nm with a standard deviation of less than +/−25% by electron microscopy. In one embodiment, the triblock copolymer-coated metallic nanoparticle seeds have a median maximum particle diameter size of between 1 nm and 20 nm with a standard deviation of less than +/−20% by electron microscopy. In one embodiment, the triblock copolymer-coated metallic nanoparticle seeds have a median maximum particle diameter size of between 1 nm and 20 nm with a standard deviation of less than +/−15% by electron microscopy. In one embodiment, the triblock copolymer-coated metallic nanoparticle seeds have a median maximum particle diameter size of between 1 nm and 20 nm with a standard deviation of less than +/−10% by electron microscopy. In one embodiment, the triblock copolymer-coated metallic nanoparticle seeds have a median maximum particle diameter size of between 1 nm and 20 nm with a standard deviation of less than +/−5% by electron microscopy. In one embodiment, the triblock copolymer-coated metallic nanoparticle seeds have a median maximum particle diameter size of between 5 nm and 15 nm with a standard deviation of less than +/−25% by electron microscopy. In one embodiment, the triblock copolymer-coated metallic nanoparticle seeds have a median maximum particle diameter size of between 5 nm and 15 nm with a standard deviation of less than +/−20% by electron microscopy. In one embodiment, the triblock copolymer-coated metallic nanoparticle seeds have a median maximum particle diameter size of between 5 nm and 15 nm with a standard deviation of less than +/−15% by electron microscopy. In one embodiment, the triblock copolymer-coated metallic nanoparticle seeds have a median maximum particle diameter size of between 5 nm and 15 nm with a standard deviation of less than +/−10% by electron microscopy. In one embodiment, the triblock copolymer-coated metallic nanoparticle seeds have a median maximum particle diameter size of between 5 nm and 15 nm with a standard deviation of less than +/−5% by electron microscopy. In one embodiment, the triblock copolymer-coated metallic nanoparticle seeds have a median maximum particle diameter size of between 8 nm and 12 nm with a standard deviation of less than +/−25% by electron microscopy. In one embodiment, the triblock copolymer-coated metallic nanoparticle seeds have a median maximum particle diameter size of between 8 nm and 12 nm with a standard deviation of less than +/−20% by electron microscopy. In one embodiment, the triblock copolymer-coated metallic nanoparticle seeds have a median maximum particle diameter size of between 8 nm and 12 nm with a standard deviation of less than +/−15% by electron microscopy. In one embodiment, the triblock copolymer-coated metallic nanoparticle seeds have a median maximum particle diameter size of between 8 nm and 12 nm with a standard deviation of less than +/−10% by electron microscopy. In one embodiment, the triblock copolymer-coated metallic nanoparticle seeds have a median maximum particle diameter size of between 8 nm and 12 nm with a standard deviation of less than +/−5% by electron microscopy. In one embodiment, the triblock copolymer-coated metallic nanoparticle seeds have a median maximum particle diameter size of 10 nm with a standard deviation of +/−1 nm by electron microscopy. In one embodiment, the triblock copolymer-coated metallic nanoparticle seeds have a number density of between $0.1 \times 10^{11}$ particles/mL and $10 \times 10^{11}$ particles/mL In another embodiment, the triblock copolymer-coated metallic nanoparticle seeds have a number density of between $0.5 \times 10^{11}$ particles/mL and $5 \times 10^{11}$ particles/mL In another embodiment, the triblock copolymer-coated metallic nanoparticle seeds have a number density of between $1 \times 10^{11}$ particles/mL and $5 \times 10^{11}$ particles/mL In one embodiment, the triblock copolymer-coated metallic nanoparticle seeds have a number density of $3 \times 10^{11}$ particles/mL In one embodiment, the triblock copolymer-coated metallic nanoparticle seeds having the narrow particle size distribution according to the present invention are produced according to the method for producing triblock copolymer-coated metallic nanoparticle seeds according to the present invention.

In one embodiment, the triblock copolymer portion of the triblock copolymer-coated metallic nanoparticle seeds is selected from the group consisting of one or more than one of L31 (MW 1100), L43 (MW 1850), L44 (MW 2200), L62 (MW 2500), P84 (MW 4200), P85 (MW 4600), P123 (MW 5760), F68 (MW 8400), F88 (MW 11400), F127 (MW 12600), F108 (MW 14600), and a combination of the preceding. In a preferred embodiment, the triblock copolymer portion of the triblock copolymer-coated metallic nanoparticle seeds comprises F127 (12600). In one embodiment, the metallic portion comprises a metal forming the metallic moiety in transition metals and their oxides selected from the group consisting of Ag, $Bi_2O_3$, CuO, $Fe_xO_y$, NiO, $TiO_2$ and ZnO. In a preferred embodiment, the metallic portion of the triblock copolymer-coated metallic nanoparticle seeds comprises gold.

According to one embodiment of the present invention, there is provided a method for producing triblock copolymer-coated metallic nanoparticles which increases the size and shape homogeneity of the triblock copolymer-coated metallic nanoparticles as compared to triblock copolymer-coated metallic nanoparticles produced by currently known methods, where the triblock copolymer-coated metallic nanoparticles comprise a triblock copolymer portion and a metallic portion. The method for producing triblock copolymer-coated metallic nanoparticles comprises: a) providing metallic nanoparticle seeds made according to the present invention, providing triblock copolymers, and providing metallic substrate comprising a metal; b) making a solution of the metallic nanoparticle seeds and the triblock copolymers; c) adding the metallic substrate to the solution; and d) chemically reducing the metallic substrate in the presence of the triblock copolymers and metallic nanoparticle seeds, thereby producing the triblock copolymer-coated metallic nanoparticles.

In one embodiment, the triblock copolymer portion of the triblock copolymer-coated metallic nanoparticles is selected from the group consisting of one or more than one of L31 (MW 1100), L43 (MW 1850), L44 (MW 2200), L62 (MW 2500), P84 (MW 4200), P85 (MW 4600), P123 (MW 5760), F68 (MW 8400), F88 (MW 11400), F127 (MW 12600), F108 (MW 14600), and a combination of the preceding. In a preferred embodiment, the triblock copolymer portion of the triblock copolymer-coated metallic nanoparticles comprises F127 (12600). In one embodiment, the metallic portion comprises a metal forming the metallic moiety in transition metals and their oxides selected from the group consisting of Ag, $Bi_2O_3$, CuO, $Fe_xO_y$, NiO, $TiO_2$ and ZnO. In a preferred embodiment, the metallic portion of the triblock copolymer-coated metallic nanoparticle seeds comprises gold.

The method for producing triblock copolymer-coated metallic nanoparticles comprises providing triblock copolymer-coated metallic nanoparticle seeds produced according to the present invention.

The method for producing triblock copolymer-coated metallic nanoparticles comprises providing triblock copolymers. In one embodiment, the triblock copolymers provided are selected from the group consisting of one or more than one of L31 (MW 1100), L43 (MW 1850), L44 (MW 2200), L62 (MW 2500), P84 (MW 4200), P85 (MW 4600), P123 (MW 5760), F68 (MW 8400), F88 (MW 11400), F127 (MW 12600), F108 (MW 14600), and a combination of the preceding. In a preferred embodiment, the triblock copolymers provided comprises F127 (12600). The triblock copolymers provided can be made according to techniques known to those with skill in the art, or can be purchased from a variety of commercially available sources, such as, for example, Sigma-Aldrich, Milwaukee, Wis. US.

The method further comprises providing metallic substrate comprising a metal. In one embodiment, the metal is selected from the group consisting of Ag, Au, Bi, Cu, Fe, Ni, Ti and Zn. In a preferred embodiment, the metallic substrate is a salt of the metal. In one embodiment, the metallic substrate is selected from the group consisting of $AgNO_3$, $CuBr_2$, $CuCl_2$, $CuF_2$, $CuI_2$, $CuSO_4$ and $HAuCl_4$. In a preferred embodiment, the metallic substrate is $HAuCl_4$. The metallic substrate provided can be purchased commercially, such as, for example, from Sigma-Aldrich, Milwaukee, Wis. US. In another embodiment, the metallic substrate is made according to techniques known to those with skill in the art.

Next, the method comprises making a solution of the metallic nanoparticle seeds, the triblock copolymers, and the metallic substrate. In one embodiment, making the solution comprises adding the metallic nanoparticle seeds made according to the present invention, and one or more than one high molecular weight triblock copolymer (MW>4000), to water. In one embodiment, the one or more than one high molecular weight triblock copolymer is selected from the group consisting of one or more than one of P84 (MW 4200), P85 (MW 4600), P123 (MW 5760), F68 (MW 8400), F88 (MW 11400), F127 (MW 12600), F108 (MW 14600), and a combination of the preceding. In a preferred embodiment, the water is deionized water. As an example, the solution can be made by dissolving the high molecular weight triblock copolymers in deionized water (Milli-Q water; Millipore, Billerica, Mass. US) to give a final concentration in (weight/volume) % of between 1% (1 g/100 mL) and 5% (5 g/100 mL) Next, metallic nanoparticle seeds are added to the solution to a final concentration of between 0.1 nM to 1 nM, such as, for example, adding 100 µL of metallic nanoparticle seeds to 900 µL of solution to make 1 mL solution. In one embodiment, the method further comprises adding one or more than one low molecular weight triblock copolymer (MW≤2500) to the solution. The combination of high molecular weight triblock copolymers and low molecular weight triblock copolymers advantageously produce an additional level of control over the triblock copolymer phase behavior, as will be understood by those with skill in the art with respect to this disclosure. In one embodiment, the one or more than one low molecular weight triblock copolymer added to the solution is selected from the group consisting of L31 (MW 1100), L43 (MW 1850), L44 (MW 2200), L62 (MW 2500), and a combination of the preceding. As an example, the solution with the low molecular weight triblock copolymers can be made using F68 as the high molecular weight triblock copolymer and L31 as the low molecular weight triblock copolymer. As an example, the solution can be made by dissolving 10 mL of 50% w/v (50 g/100 mL) F68 and 10 mL L31 in 100 mL of deionized water (Milli-Q water; Millipore, Billerica, Mass. US) to give a final concentration of 8 mM L31 and 4 mM F68. This mixture corresponds to an EO:PO molar ratio of about 0.7. Next, metallic nanoparticle seeds are added to the solution to a final concentration of 0.1 nM to 1 nM, such as, for example, adding 100 µL of metallic nanoparticle seeds to 900 µL of solution to make 1 mL solution. Advantageously, the cloud point (CP) (where the solution phase separates of stock) can be reduced from above 100° C. for aqueous F68 binary mixtures to about 30° C. for aqueous L31/F68 ternary mixtures. The solution was incubated at 25° C. for about 15 minutes.

Then, the method comprises adding the metallic substrate to the solution. By way of example, 100 mM $HAuCl_4$ was added to the solution to give a final Au(III) concentration of 1 mM, thereby producing the triblock copolymer-coated metallic nanoparticles.

Next, the method comprises chemically reducing the metallic substrate in the presence of the triblock copolymers and metallic nanoparticle seeds, thereby producing the triblock copolymer-coated metallic nanoparticles. Increasing the seed concentration reduced the average particle size. Without using the metallic nanoparticle seeds, the triblock copolymer-coated metallic nanoparticles produced were heterogeneous. An examination of the volume weighted DLS particle size distribution and electron microscopy showed that increasing the seed concentration decreases the mean hydrodynamic diameters from (1370±290) to (86±12) nm in the larger triblock copolymer-coated metallic nanoparticles population. Similarly, the mean hydrodynamic diameters decreased from (117±37) to (10±1) nm in the smaller triblock copolymer-coated metallic nanoparticles. Comparable particle size distributions were also obtained for about 4 mM F68 aqueous solutions.

In another embodiment, the method further comprises monitoring the production of the coated metallic nanoparticles. In a preferred embodiment, monitoring is performed by observing the changes in the absorption spectra using a UV-vis spectrometer (such as, for example, a Varian Cary 300, LabWrench, Midland, ON Canada) fitted with temperature control at 25±1° C. The growth kinetics within the first 30 minutes of growth are monitored by UV-vis spectroscopy by monitoring the evolution of the precursor and gold nanoparticles peaks at 320 and 540 nm, respectively. The $AuCl_4$ concentration is estimated from the absorption bands by the use of extinction coefficients: 9823 $M^{-1}$ $cm^{-1}$ and 5400 $M^{-1}$ $cm^{-1}$, at 240 and 320 nm, respectively. Dynamic light scattering (DLS) measurements are made (such as, for example, using a model NICOMP 370 submicron particle sizer, Particle Sizing Systems, Santa Barbara, Calif. US) at a He—Ne laser wavelength of 632 nm with a power output of 60 mW. For dynamic light scattering measurements, samples are centrifuged (10,600×g) to remove excess surfactant and suspended in water.

In another embodiment, the method further comprises characterizing the triblock copolymer-coated gold nanoparticles produced according to the present invention. In one embodiment, characterizing comprises measuring the size of the triblock copolymer-coated metallic nanoparticles using scanning transmission electron microscopy using techniques known to those with skill in the art, as will be understood by those with skill in the art with respect to this disclosure. For example, in one embodiment, characterization using scanning transmission electron microscopy comprises preparing the samples by centrifuging (10,600×g) the samples twice to remove excess polymer, and then suspending the centrifuged sample in water. Next, a drop of the suspended sample is mounted on a carbon-coated Cu grid (such as, for example, 200 mesh, Ted Pella, Inc., Redding, Calif. US) and allowed to air dry. Then, field emission scanning electron microscopy (FESEM) analysis is performed, using techniques known to those with skill in the art, as will be understood by those with skill in the art with respect to this disclosure, such as, for example, using a Gemini® FIB/FESEM instrument (Carl Zeiss NTS GMBH, Oberkochen, Germany) with scanning transmission electron microscopy (STEM) capabilities at an operating voltage of 20 kV. In another embodiment, characterizing comprises imaging the triblock copolymer-coated metallic nanoparticles using atomic force microscopy (AFM), using techniques known to those with skill in the art, as will be understood by those with skill in the art with respect to this disclosure. For example, in one embodiment, characterization using atomic force microscopy comprises using a MultiMode® 8 Atomic Force Microscope (Bruker Nano, Inc. Santa Barbara, Calif. US) in the Peak Force Tapping® (Bruker Nano, Inc. Santa Barbara, Calif. US) mode and using ScanAsyst® (Bruker Nano, Inc. Santa Barbara, Calif. US) (k=0.4 $Nm^{-1}$, f=70 kHz) air probes. Automated feedback parameter optimization is achieved using ScanAsyst®. The Peak Force Tapping® mode modulates the cantilever at ca 2 kHz at each pixel of the image where the feedback is based on the interaction force each time the tip taps the sample.

According to another embodiment of the present invention, there is provided a quantity of triblock copolymer-coated metallic nanoparticles. In one embodiment, the triblock copolymer-coated metallic nanoparticles have a median maximum particle diameter size standard deviation of +/−25% of the median maximum particle diameter size by electron microscopy. In one embodiment, the triblock copolymer-coated metallic nanoparticles have a median maximum particle diameter size standard deviation of +/−20% of the median maximum particle diameter size by electron microscopy. In one embodiment, the triblock copolymer-coated metallic nanoparticles have a median maximum particle diameter size standard deviation of +/−15% of the median maximum particle diameter size by electron microscopy. In one embodiment, the triblock copolymer-coated metallic nanoparticles have a median maximum particle diameter size standard deviation of +/−10% of the median maximum particle diameter size by electron microscopy. In one embodiment, the triblock copolymer-coated metallic nanoparticles have a median maximum particle diameter size standard deviation of +/−5% of the median maximum particle diameter size by electron microscopy. In one embodiment, the triblock copolymer-coated metallic nanoparticles have a median maximum particle diameter size of between 30 nm and 300 nm with a standard deviation of +/−25% by electron microscopy. In one embodiment, the triblock copolymer-coated metallic nanoparticles have a median maximum particle diameter size of between 30 nm and 300 nm with a standard deviation of +/−20% by electron microscopy. In one embodiment, the triblock copolymer-coated metallic nanoparticles have a median maximum particle diameter size of between 30 nm and 300 nm with a standard deviation of +/−15% by electron microscopy. In one embodiment, the triblock copolymer-coated metallic nanoparticles have a median maximum particle diameter size of between 30 nm and 300 nm with a standard deviation of +/−10% by electron microscopy. In one embodiment, the triblock copolymer-coated metallic nanoparticles have a median maximum particle diameter size of between 30 nm and 300 nm with a standard deviation of +/−5% by electron microscopy. In one embodiment, the triblock copolymer-coated metallic nanoparticles have a median maximum particle diameter size of between 30 nm and 100 nm with a standard deviation of +/−25% by electron microscopy. In one embodiment, the triblock copolymer-coated metallic nanoparticles have a median maximum particle diameter size of between 30 nm and 100 nm with a standard deviation of +/−20% by electron microscopy. In one embodiment, the triblock copolymer-coated metallic nanoparticles have a median maximum particle diameter size of between 30 nm and 100 nm with a standard deviation of +/−15% by electron microscopy. In one embodiment, the triblock copolymer-coated metallic nanoparticles have a median maximum particle diameter size of between 30 nm and 100 nm with a standard deviation of +/−10% by electron microscopy. In one embodiment, the triblock copolymer-coated metallic nanoparticles have a median maximum particle diameter size of between 30 nm and 100 nm with a standard deviation of +/−5% by electron microscopy. In one embodiment, the triblock copolymer-coated metallic nanoparticles have a median maximum particle diameter size of between 40 nm and 60 nm with a standard deviation of +/−25% by electron microscopy. In one embodiment, the triblock copolymer-coated metallic nanoparticles have a median maximum particle diameter size of between 40 nm and 60 nm with a standard deviation of +/−20% by electron microscopy. In one embodiment, the triblock copolymer-coated metallic nanoparticles have a median maximum particle diameter size of between 40 nm and 60 nm with a standard deviation of +/−15% by electron microscopy. In one embodiment, the triblock copolymer-coated metallic nanoparticles have a median maximum particle diameter size of between 40 nm and 60 nm with a standard deviation of +/−10% by electron microscopy. In one embodiment, the triblock copolymer-coated metallic nanoparticles have a median maximum particle diameter size of between 40 nm and 60 nm with a standard deviation of +/−5% by electron microscopy. In one embodiment, the number density of the triblock copolymer-coated metallic nanoparticles is between $0.1 \times 10^{10}$ particles/cm$^3$ and $10 \times 10^{10}$ particles/cm$^3$. In one embodiment, the number density of the triblock copolymer-coated metallic nanoparticles is between $0.5 \times 10^{10}$ particles/cm$^3$ and $5 \times 10^{10}$ particles/cm$^3$. In one embodiment, the number density of the triblock copolymer-coated metallic nanoparticles is between $1 \times 10^{10}$ particles/cm$^3$ and $5 \times 10^{10}$ particles/cm$^3$. In one embodiment, the number density of the triblock copolymer-coated metallic nanoparticles is $1 \times 10^{10}$ particles/cm$^3$. In one embodiment, the triblock copolymer-coated metallic nanoparticles having the narrow particle size distribution are produced according to the method for producing triblock copolymer-coated metallic nanoparticles according to the present invention.

In one embodiment, the triblock copolymer portion of the triblock copolymer-coated metallic nanoparticles is selected from the group consisting of one or more than one of L31 (MW 1100), L43 (MW 1850), L44 (MW 2200), L62 (MW 2500), P84 (MW 4200), P85 (MW 4600), P123 (MW 5760), F68 (MW 8400), F88 (MW 11400), F127 (MW 12600), F108 (MW 14600), and a combination of the preceding. In a preferred embodiment, the triblock copolymer portion of the triblock copolymer-coated metallic nanoparticles comprises F127 (12600). In one embodiment, the metallic portion comprises a metal forming the metallic moiety in transition metals and their oxides selected from the group consisting of Ag, Bi$_2$O$_3$, CuO, Fe$_x$O$_y$, NiO, TiO$_2$ and ZnO. In a preferred embodiment, the metallic portion of the triblock copolymer-coated metallic nanoparticles comprises gold.

According to another embodiment of the present invention, there is provided a method for producing modified metallic nanoparticles, where the modified metallic nanoparticles comprise a ligand portion and a metallic portion. In one embodiment, the ligand portion comprises a small organic molecule. In a preferred embodiment, the ligand portion is selected from the group consisting of one or more than one antibody, metal, peptide, protein, oligonucleotide, thiolated DNA and a combination of the preceding; however, other ligand portions can be used, as will be understood by those with skill in the art with respect to this disclosure. In a preferred embodiment, the metallic portion of the modified metallic nanoparticles comprises gold. The method comprises providing triblock copolymer-coated metallic nanoparticles according to the present invention. Next, the method comprises replacing the triblock copolymer portion with the ligand according to techniques known to those with skill in the art. For example, replacing the triblock copolymer portion with the ligand triblock copolymer portion can comprise one or more than one technique selected from the group consisting of in-situ interfacial reaction, overlayer growth and surface overlayer exchange, though any other suitable method can be used as will be understood by those with skill in the art with respect to this disclosure.

According to another embodiment of the present invention, there is provided a quantity of modified metallic nanoparticles. In one embodiment, the modified metallic nanoparticles have a median maximum particle diameter size standard deviation of +/−25% of the median maximum particle diameter size by electron microscopy. In one embodiment, the modified metallic nanoparticles have a median maximum particle diameter size standard deviation of +/−20% of the median maximum particle diameter size by electron microscopy. In one embodiment, the modified metallic nanoparticles have a median maximum particle diameter size standard deviation of +/−15% of the median maximum particle diameter size by electron microscopy. In one embodiment, the modified metallic nanoparticles have a median maximum particle diameter size standard deviation of +/−10% of the median maximum particle diameter size by electron microscopy. In one embodiment, the modified metallic nanoparticles have a median maximum particle diameter size standard deviation of +/−5% of the median maximum particle diameter size by electron microscopy. In one embodiment, the modified metallic nanoparticles have a median maximum particle diameter size of between 30 nm and 300 nm with a standard deviation of +/−25% by electron microscopy. In one embodiment, the modified metallic nanoparticles have a median maximum particle diameter size of between 30 nm and 300 nm with a standard deviation of +/−20% by electron microscopy. In one embodiment, the modified metallic nanoparticles have a median maximum particle diameter size of between 30 nm and 300 nm with a standard deviation of +/−15% by electron microscopy. In one embodiment, the modified metallic nanoparticles have a median maximum particle diameter size of between 30 nm and 300 nm with a standard deviation of +/−10% by electron microscopy. In one embodiment, the modified metallic nanoparticles have a median maximum particle diameter size of between 30 nm and 300 nm with a standard deviation of +/−5% by electron microscopy. In one embodiment, the modified metallic nanoparticles have a median maximum particle diameter size of between 30 nm and 100 nm with a standard deviation of +/−25% by electron microscopy. In one embodiment, the modified metallic nanoparticles have a median maximum particle diameter size of between 30 nm and 100 nm with a standard deviation of +/−20% by electron microscopy. In one embodiment, the modified metallic nanoparticles have a median maximum particle diameter size of between 30 nm and 100 nm with a standard deviation of +/−15% by electron microscopy. In one embodiment, the modified metallic nanoparticles have a median maximum particle diameter size of between 30 nm and 100 nm with a standard deviation of +/−10% by electron microscopy. In one embodiment, the modified metallic nanoparticles have a median maximum particle diameter size of between 30 nm and 100 nm with a standard deviation of +/−5% by electron microscopy. In one embodiment, the modified metallic nanoparticles have a median maximum particle diameter size of between 40 nm and 60 nm with a standard deviation of +/−25% by electron microscopy. In one embodiment, the modified metallic nanoparticles have a median maximum particle diameter size of between 40 nm and 60 nm with a standard deviation of +/−20% by electron microscopy. In one embodiment, the modified metallic nanoparticles have a median maximum particle diameter size of between 40 nm and 60 nm with a standard deviation of +/−15% by electron microscopy. In one embodiment, the modified metallic nanoparticles have a median maximum particle diameter size of between 40 nm and 60 nm with a standard deviation of +/−10% by electron microscopy. In one embodiment, the modified metallic nanoparticles have a median maximum particle diameter size of between 40 nm and 60 nm with a standard deviation of +/−5% by electron microscopy. In one embodiment, the number density of the modified metallic nanoparticles is between $0.1 \times 10^{10}$ particles/cm$^3$ and $10 \times 10^{10}$ particles/cm$^3$. In one embodiment, the number density of the modified metallic nanoparticles is between $0.5 \times 10^{10}$ particles/cm$^3$ and $5 \times 10^{10}$ particles/cm$^3$. In one embodiment, the number density of the modified metallic nanoparticles is between $1\times10^{10}$ particles/$cm^3$ and $5\times10^{10}$ particles/$cm^3$. In one embodiment, the number density of the modified metallic nanoparticles is between $1\times10^{10}$ particles/$cm^3$. In one embodiment, the modified metallic nanoparticles having the narrow particle size distribution are produced according to the method for producing modified metallic nanoparticles according to the present invention.

According to another embodiment of the present invention, there is provided a method of using triblock copolymer-coated metallic nanoparticles, where the method comprises providing the triblock copolymer-coated metallic nanoparticles according to the present invention. According to another embodiment of the present invention, there is provided a method of using modified metallic nanoparticles, where the method comprises providing the modified metallic nanoparticles according to the present invention.

According to another embodiment of the present invention, there is provided a method of treating a patient for a condition or disease. The method comprises, first determining that the patient has a condition or disease suitable for treatment by the administration of the triblock copolymer-coated metallic nanoparticles. Next, the method comprises providing triblock copolymer-coated metallic nanoparticles according to the present invention. Then, the method comprises administering to the patient one or more than one dose of the triblock copolymer-coated metallic nanoparticles by a route, thereby treating the condition or disease. In one embodiment, the patient is a human. In one embodiment, the one or more than one dose administered is between 0.01 ng and 1 gram. In another embodiment, the one or more than one dose administered is between 0.01 ng and 10,000 mg. In another embodiment, the one or more than one dose administered is between 1 ng and 10,000 mg. In another embodiment, the one or more than one dose administered is between 0.1 mg and 10,000 mg. In one embodiment, the one or more than one dose administered is a plurality of doses. In one embodiment, the plurality of doses is two doses. In another embodiment, the plurality of doses is three doses. In another embodiment, the plurality of doses is four doses. In another embodiment, the plurality of doses is more than four doses. In one embodiment, the plurality of doses is administered between one hour and seventy-two hours apart. In another embodiment, the plurality of doses is administered between one hour and thirty-six hours apart. In another embodiment, the plurality of doses is administered between one hour and twenty-four hours apart. In one embodiment, the route is selected from the group consisting of intrarectal, intramuscular, intraperitoneal, intrathecal, intravenous and oral. In one embodiment, the condition or disease is cancer and administering the triblock copolymer-coated metallic nanoparticles decreases the toxicity of radiotherapy being used to treat the cancer. In one embodiment, the ligand portion of the triblock copolymer-coated metallic nanoparticles is a delivery vehicle for biologically active agents. In one embodiment, determining that the patient has a condition or disease suitable for treatment by the administration of the triblock copolymer-coated metallic nanoparticles comprises diagnosing the patient with a condition or disease suitable for treatment by the present method. In one embodiment, diagnosing the patient comprises performing one or more than one of action selected from the group consisting of performing a physical examination, performing a non-invasive imaging examination (such as magnetic resonance imaging, computerized tomography and ultrasound), and identifying one or more than one marker for the condition or disease in the blood or other body fluid of the patient. In another embodiment, identifying the patient comprises consulting patient records to determine if the patient has a condition or disease suitable for treatment by the present method.

According to another embodiment of the present invention, there is provided a method of treating a patient for a condition or disease. The method comprises, first providing modified metallic nanoparticles according to the present invention. Next, the method comprises determining that the patient has a condition or disease suitable for treatment by the administration of the modified metallic nanoparticles. Then, the method comprises administering to the patient one or more than one dose of the modified metallic nanoparticles by a route, thereby treating the condition or disease. In one embodiment, the patient is a human. In one embodiment, the one or more than one dose administered is between 0.01 ng and 1 gram. In another embodiment, the one or more than one dose administered is between 0.01 ng and 10,000 mg. In another embodiment, the one or more than one dose administered is between 1 ng and 10,000 mg. In another embodiment, the one or more than one dose administered is between 0.1 mg and 10,000 mg. In one embodiment, the one or more than one dose administered is a plurality of doses. In one embodiment, the plurality of doses is two doses. In another embodiment, the plurality of doses is three doses. In another embodiment, the plurality of doses is four doses. In another embodiment, the plurality of doses is more than four doses. In one embodiment, the plurality of doses is administered between one hour and seventy-two hours apart. In another embodiment, the plurality of doses is administered between one hour and thirty-six hours apart. In another embodiment, the plurality of doses is administered between one hour and twenty-four hours apart. In one embodiment, the route is selected from the group consisting of intrarectal, intramuscular, intraperitoneal, intrathecal, intravenous and oral. In one embodiment, the condition or disease is cancer and administering the modified metallic nanoparticles decreases the toxicity of radiotherapy being used to treat the cancer. In one embodiment, the ligand portion of the modified metallic nanoparticles is a delivery vehicle for biologically active agents. In another embodiment, the ligand portion of the modified metallic nanoparticles is N-caproyl-penta-arginine amide (Cap-$R_5$—$NH_2$) (fatty acid) terminated peptide. In one embodiment, determining that the patient has a condition or disease suitable for treatment by the administration of the modified metallic nanoparticles comprises diagnosing the patient with a condition or disease suitable for treatment by the present method. In one embodiment, diagnosing the patient comprises performing one or more than one of action selected from the group consisting of performing a physical examination, performing a non-invasive imaging examination (such as magnetic resonance imaging, computerized tomography and ultrasound), and identifying one or more than one marker for the condition or disease in the blood or other body fluid of the patient. In another embodiment, identifying the patient comprises consulting patient records to determine if the patient has a condition or disease suitable for treatment by the present method.

According to another embodiment of the present invention, there is provided a pharmaceutical suitable for treating a patient with a condition or disease. In one embodiment, the pharmaceutical comprises triblock copolymer-coated metallic nanoparticles according to the present invention. In another embodiment, the pharmaceutical comprises modified metallic nanoparticles according to the present invention. The pharmaceutical additionally comprises one or more than one substance selected from the group consisting of a binder, a coloring chemical and a flavoring chemical, as will be understood by those with skill in the art with respect to this disclosure.

Although the present invention has been discussed in considerable detail with reference to certain preferred embodiments, other embodiments are possible. Therefore, the scope of the appended claims should not be limited to the description of preferred embodiments contained in this disclosure. All references cited herein are incorporated by reference in their entirety.

What is claimed is:

1. A method for producing triblock copolymer-coated gold nanoparticle seeds which increases the size and shape homogeneity of the triblock copolymercoated gold nanoparticle seeds, where the triblock copolymer-coated gold nanoparticle seeds consist of triblock copolymers and gold, the method comprising:
   a) providing triblock copolymers;
   b) providing metallic substrate comprising gold, the gold having at least two oxidation states, a lowest oxidation state and a higher oxidation state, where at least some of the gold is in the higher oxidation state;
   c) making a solution of the triblock copolymers and water;
   d) adding a reducing agent selected from the group consisting of L-ascorbic acid or an analog of L-ascorbic acid to the solution, where the reducing agent reduces gold from a higher oxidation state to a lowest oxidation state of the gold, or to an oxidation state that is unstable and that reverts to a lowest oxidation state of the gold without further chemical modification;
   e) after step d) adding the metallic substrate to the solution thereby creating a concentration of the metallic substrate in the solution; and
   f) allowing the solution to remain a sufficient time to allow formation of the triblock copolymer-coated gold nanoparticle seeds consisting of triblock copolymers and gold;
   where all of the gold in the triblock copolymer-coated gold nanoparticle seeds is in the lowest oxidation state;
   where the triblock copolymer-coated gold nanoparticle seeds have a median maximum particle diameter size of between 5 nm and 15 nm; and
   where the triblock copolymer-coated gold nanoparticle seeds have a median maximum particle diameter size standard deviation of +/−15% of the median maximum particle diameter size by electron microscopy.

2. The method of claim 1, where the triblock copolymers are selected from the group consisting of one or more than one of L31 (MW 1100), L43 (MW 1850), L44 (MW 2200), L62 (MW 2500), P84 (MW 4200), P85 (MW 4600), P123 (MW 5760), F68 (MW 8400), F88 (MW 11400), F127 (MW 12600), F108 (MW 14600), and a combination of the preceding.

3. The method of claim 1, where the triblock copolymers comprise F127 (12600).

4. The method of claim 1, where the metallic substrate is $HAuCl_4$.

5. The method of claim 1, where the triblock copolymers comprise one or more than one high molecular weight triblock copolymer (MW>4000).

6. The method of claim 5, where the one or more than one high molecular weight triblock copolymer is selected from the group consisting of one or more than one of P84 (MW 4200), P85(MW 4600), P123 (MW 5760), F68 (MW 8400), F88 (MW 11400), F127 (MW 12600), F108 (MW 14600), and a combination of the preceding.

7. The method of claim 1, further comprising adding one or more than one low molecular weight triblock copolymer (MW~2500) to the solution.

8. The method of claim 7, where the one or more than one low molecular weight triblock copolymer added to the solution is selected from the group consisting of L31 (MW 1100), L43 (MW 1850), L44 (MW 2200), L62 (MW 2500), and a combination of the preceding.

9. The method of claim 1, where the analog of L-ascorbic acid is selected from the group consisting of ascorbyl palmitate and magnesium ascorbyl phosphate.

10. The method of claim 1, where the reducing agent is added to the solution in a higher concentration than the concentration of the metallic substrate in the solution.

11. The method of claim 1, where the reducing agent is added to the solution at a concentration of at least 1.5 times the concentration of the metallic substrate.

12. The method of claim 1, where the reducing agent is added to the solution at a concentration of at least 2 times the concentration of the metallic substrate.

13. The method of claim 1, where the reducing agent is added to the solution at a concentration of at least 2.5 times the concentration of the metallic substrate.

14. The method of claim 1, where the reducing agent is added to the solution at a concentration of at least 3 times the concentration of the metallic substrate.

15. The method of claim 1, further comprising harvesting the triblock copolymer-coated gold nanoparticle seeds.

16. The method of claim 1, further comprising characterizing the triblock copolymer-coated gold nanoparticle seeds, wherein the triblock copolymer-coated gold nanoparticle seeds are characterized by electron microscopy, scanning transmission electron microscopy, or atomic force microscopy.

17. The method of claim 1, where the triblock copolymer-coated gold nanoparticle seeds have a median maximum particle diameter size of 10 nm with a standard deviation of +/−1 nm by electron microscopy.

18. The method of claim 1, where the triblock copolymer-coated gold nanoparticle seeds have a number density of between $0.1 \times 10^{11}$ particles/mL and $10 \times 10^{11}$ particles/mL.

19. A method for producing triblock copolymer-coated metallic nanoparticles which increases the size and shape homogeneity of the triblock copolymer-coated metallic nanoparticles, where the triblock copolymer-coated metallic nanoparticles comprise a triblock copolymer portion and a metallic portion, the method comprising:
   a) providing the triblock copolymer-coated gold nanoparticle seeds made according to the method of claim 1, providing triblock copolymers, and providing metallic substrate comprising a metal;
   b) making a solution of the triblock copolymer-coated gold nanoparticle seeds and the triblock copolymers;
   c) adding the metallic substrate to the solution; and
   d) chemically reducing the metallic substrate in the presence of the triblock copolymers and triblock copolymer-coated gold nanoparticle seeds to produce the triblock copolymercoated metallic nanoparticles.

20. The method of claim 19, where the triblock copolymer portion of the triblock copolymer-coated metallic nanoparticles is selected from the group consisting of one or more than one of L31 (MW 1100), L43 (MW 1850), L44 (MW 2200), L62 (MW 2500), P84 (MW 4200), P85 (MW 4600), P123 (MW 5760), F68 (MW 8400), F88 (MW 11400), F127 (MW 12600), F108 (MW 14600), and a combination of the preceding.

21. The method of claim 19, where the triblock copolymer portion of the triblock copolymer-coated metallic nanoparticles comprises F127 (12600).

22. The method of claim 19, where the metallic portion comprises a metal forming the metallic moiety in transition metals and their oxides selected from the group consisting of Ag, $Bi_2O_3$, CuO, $Fe_xO_y$, NiO, $TiO_2$ and ZnO.

23. The method of claim 19, where the triblock copolymers provided are selected from the group consisting of one or more than one of L31 (MW 1100), L43 (MW 1850), L44 (MW 2200), L62 (MW 2500), P84 (MW 4200), P85 (MW 4600), P123 (MW 5760), F68 (MW 8400), F88 (MW 11400), F127 (MW 12600), F108 (MW 14600), and a combination of the preceding.

24. The method of claim 19, where the triblock copolymers comprise F127 (12600).

25. The method of claim 19, where the metal is selected from the group consisting of Ag, Au, Bi, Cu, Fe, Ni, Ti and Zn.

26. The method of claim 19, where the metallic substrate is a salt of the metal.

27. The method of claim 19, where the metallic substrate is selected from the group consisting of $AgNO_3$, $CuBr_2$, $CuCl_2$, $CuF_2$, $CuI_2$, $CuSO_4$ and $HAuCl_4$.

28. The method of claim 19, where the metallic substrate is $HAuCl_4$.

29. The method of claim 19, where the triblock copolymers comprise one or more than one high molecular weight triblock copolymer (MW>4000).

30. The method of claim 29, where the one or more than one high molecular weight triblock copolymer is selected from the group consisting of one or more than one of P84 (MW 4200), P85 (MW 4600), P123 (MW 5760), F68 (MW 8400), F88 (MW 11400), F127 (MW 12600), F108 (MW 14600), and a combination of the preceding.

31. The method of claim 29, where the triblock copolymers further comprise one or more than one low molecular weight triblock copolymers (MW≤2500).

32. The method of claim 31, where the one or more than one low molecular weight triblock copolymer is selected from the group consisting of L31 (MW 1100), L43 (MW 1850), L44 (MW 2200), L62 (MW 2500), and a combination of the preceding.

33. The method of claim 19, further comprising monitoring the production of the triblock copolymer-coated metallic nanoparticles.

34. The method of claim 19, further comprising characterizing the triblock copolymer-coated metallic nanoparticles.

35. A method for producing modified metallic nanoparticles, where the modified metallic nanoparticles comprise a ligand portion and a metallic portion, the method comprising:
  a) producing triblock copolymer-coated gold nanoparticle seeds with increased size and shape homogeneity of the triblock copolymer-coated gold nanoparticle seeds, where the triblock copolymer-coated gold nanoparticle seeds consist of triblock copolymers and gold, through a method comprising:
    i) providing triblock copolymers;
    ii) providing metallic substrate comprising gold, the gold having at least two oxidation states, a lowest oxidation state and a higher oxidation state, where at least some of the gold is in the higher oxidation state;
    iii) making a solution of the triblock copolymers and water;
    iv) adding a reducing agent selected from the group consisting of L-ascorbic acid or an analog of L-ascorbic acid to the solution where the reducing agent reduces gold from a higher oxidation state to a lowest oxidation state of the gold, or to an oxidation state that is unstable and that reverts to a lowest oxidation state of the gold without further chemical modification;
    v) after step iv) adding the metallic substrate to the solution thereby creating a concentration of the metallic substrate in the solution; and
    vi) allowing the solution to remain a sufficient time to allow formation of the triblock copolymer-coated gold nanoparticle seeds consisting of triblock copolymers and gold;
  where all of the gold in the triblock copolymer-coated gold nanoparticle seeds is in the lowest oxidation state;
  where the triblock copolymer-coated gold nanoparticle seeds have a median maximum particle diameter size of between 5 nm and 15 nm; and
  where the triblock copolymer-coated gold nanoparticle seeds have a median maximum particle diameter size standard deviation of +/−15% of the median maximum particle diameter size by electron microscopy,
  b) providing the triblock copolymer-coated gold nanoparticle seeds with increased size and shape homogeneity of
    (a) providing triblock copolymers, and providing metallic-substrate comprising gold;
    i) making a solution of the triblock copolymer-coated gold nanoparticle seeds and the triblock copolymers;
    ii) adding the metallic substrate to the solution; and
    iii) chemically reducing the metallic substrate in the presence of the triblock copolymers and triblock copolymer-coated gold nanoparticle seeds to produce the triblock copolymer-coated gold nanoparticles;
  c) replacing the triblock copolymer portion with the ligand.

36. The method of claim 35, where the ligand portion comprises a small organic molecule.

37. The method of claim 35, where the ligand portion is selected from the group consisting of one or more than one antibody, metal, peptide, protein, oligonucleotide, thiolated DNA and a combination of the preceding.

38. The method of claim 35, where the metallic portion of the modified metallic nanoparticles comprises gold.

\* \* \* \* \*